(12) United States Patent
Rossi et al.

(10) Patent No.: US 9,775,848 B2
(45) Date of Patent: *Oct. 3, 2017

(54) TRANSDERMAL CONTRACEPTIVE HORMONES DELIVERY

(71) Applicant: Agile Therapeutics, Inc., Princeton, NJ (US)

(72) Inventors: Thomas M. Rossi, Stockton, NJ (US); Marie Foegh, Cresskill, NJ (US); Agis Kydonieus, Kendall Park, NJ (US)

(73) Assignee: Agile Therapeutics, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/925,207

(22) Filed: Oct. 28, 2015

(65) Prior Publication Data

US 2016/0106759 A1    Apr. 21, 2016

Related U.S. Application Data

(63) Continuation of application No. 13/123,021, filed as application No. PCT/US2009/059826 on Oct. 7, 2009, now Pat. No. 9,192,614.

(Continued)

(51) Int. Cl.
| | |
|---|---|
| *A61K 31/57* | (2006.01) |
| *A61K 31/565* | (2006.01) |
| *A61K 31/566* | (2006.01) |
| *A61K 9/70* | (2006.01) |
| *A61K 47/12* | (2006.01) |
| *A61K 47/14* | (2017.01) |
| *A61K 47/24* | (2006.01) |

(52) U.S. Cl.
CPC ............ *A61K 31/57* (2013.01); *A61K 9/7023* (2013.01); *A61K 9/7038* (2013.01); *A61K 9/7061* (2013.01); *A61K 9/7084* (2013.01); *A61K 31/565* (2013.01); *A61K 31/566* (2013.01); *A61K 47/12* (2013.01); *A61K 47/14* (2013.01); *A61K 47/24* (2013.01); *A61K 2300/00* (2013.01)

(58) Field of Classification Search
CPC .. A61K 2300/00; A61K 31/565; A61K 31/57; A61K 9/7061; A61K 9/7038; A61K 9/7084
See application file for complete search history.

(56) References Cited

U.S. PATENT DOCUMENTS

| | | |
|---|---|---|
| 5,252,334 A | 10/1993 | Chiang et al. |
| 5,393,529 A | 2/1995 | Hoffman et al. |

(Continued)

FOREIGN PATENT DOCUMENTS

| | | |
|---|---|---|
| CA | 2 256 365 | 11/1997 |
| CA | 2 571 377 | 2/2006 |

(Continued)

OTHER PUBLICATIONS

Henzl et al., "Avoiding Menstruation Review of Health and Lifestyle Issues", Journal of Reproductive Medicine, vol. 49, 162-174 (2004).

(Continued)

*Primary Examiner* — Isis Ghali
(74) *Attorney, Agent, or Firm* — Potter Anderson and Corroon LLP

(57) ABSTRACT

Dosing regimen for transdermal delivery of hormones comprising a monthly treatment cycle with a fixed treatment interval and a variable rest interval.

15 Claims, 3 Drawing Sheets

Related U.S. Application Data

(60) Provisional application No. 61/103,741, filed on Oct. 8, 2008.

(56) References Cited

U.S. PATENT DOCUMENTS

| | | |
|---|---|---|
| 5,418,228 A | 5/1995 | Bennink |
| 5,512,292 A | 4/1996 | Gale et al. |
| 5,552,394 A | 9/1996 | Hodgen |
| 5,583,129 A | 12/1996 | Spona et al. |
| 5,676,968 A | 10/1997 | Lipp et al. |
| 5,747,480 A | 5/1998 | Gast |
| 5,770,219 A | 6/1998 | Chiang et al. |
| 5,824,667 A | 10/1998 | Spona et al. |
| 5,858,405 A | 1/1999 | Gast |
| 5,876,746 A | 3/1999 | Jona et al. |
| 5,888,543 A | 3/1999 | Gast |
| 5,898,032 A | 4/1999 | Hodgen |
| 5,980,940 A | 11/1999 | Spona et al. |
| 6,027,749 A | 2/2000 | Schmidt-Gollwitzer et al. |
| 6,214,815 B1 | 4/2001 | Shangold et al. |
| 6,228,852 B1 | 5/2001 | Shaak |
| 6,251,956 B1 | 6/2001 | Kafrissen et al. |
| RE37,564 E | 2/2002 | Spona et al. |
| 6,451,778 B1 | 9/2002 | Gast |
| 6,479,475 B1 | 11/2002 | Gast |
| 6,500,814 B1 | 12/2002 | Hesch |
| 6,660,295 B2 | 12/2003 | Watanabe et al. |
| 6,995,149 B1 | 2/2006 | Endrikat et al. |
| 7,045,145 B1 | 5/2006 | Chien |
| RE39,861 E | 9/2007 | Hodgen |
| 7,384,650 B2 | 6/2008 | Chien |
| 2004/0053901 A1 | 3/2004 | Chien et al. |
| 2004/0142914 A1 | 7/2004 | Friedman et al. |
| 2004/0243606 A1 | 12/2004 | Hesch |
| 2005/0032764 A1 | 2/2005 | Tuba et al. |
| 2005/0064031 A1 | 3/2005 | Stockemann et al. |
| 2005/0142175 A1 | 6/2005 | Langguth et al. |
| 2005/0143359 A1 | 6/2005 | Bell et al. |
| 2005/0250747 A1 | 11/2005 | Sachse |
| 2006/0135496 A1 | 6/2006 | Diliberti et al. |
| 2006/0241091 A1 | 10/2006 | Boissonneault |
| 2006/0241092 A1 | 10/2006 | Anderson |
| 2007/0037780 A1 | 2/2007 | Ebert et al. |
| 2007/0111975 A1 | 5/2007 | Diliberti et al. |
| 2008/0025920 A1 | 1/2008 | Simes et al. |
| 2008/0241231 A1 | 10/2008 | Gonyer et al. |
| 2008/0242650 A1 | 10/2008 | Thomas |

FOREIGN PATENT DOCUMENTS

| | | |
|---|---|---|
| CA | 2 624 810 | 2/2007 |
| EP | 0 253 607 A1 | 1/1988 |
| EP | 1 541 137 A2 | 6/2005 |
| WO | WO 2005/002482 | 1/2005 |
| WO | WO 2007/001888 A2 | 1/2007 |
| WO | WO 2010/042612 A1 | 4/2010 |

OTHER PUBLICATIONS

LaGuardia et al., "Suppression of estrogen-withdrawal headache with extended transdermal contraception", Fertility and Sterility, vol. 83, 1875-1877 (2005).

Stewart et al., "Extended Use of Transdermal Norelgestromin/Ethinyl Estradiol: A Randomized Trial", Obstet. Gynecol., vol. 105, No. 6, 1389-1396 (2005).

International Search Report in PCT/US2009/059823, mailed Dec. 9, 2009.

International Search Report in PCT/US2009/059826, mailed Nov. 25, 2009.

International Search Report in PCT/US2009/059828, mailed Jan. 29, 2010.

International Search Report in PCT/US2009/028662, mailed May 12, 2010.

U.S. Appl. No. 13/123,012, filed Jul. 1, 2011.
U.S. Appl. No. 13/123,026, filed Jul. 1, 2011.
U.S. Appl. No. 13/259,425, filed Sep. 23, 2011.

TRANSDERMAL CONTRACEPTIVE HORMONES DELIVERY

CROSS-REFERENCE TO RELATED APPLICATIONS

This is a continuation of U.S. application Ser. No. 13/123,021 filed Jul. 1, 2011, which is a national entry pursuant to 35 U.S.C. §371 of PCT/US2009/059826, filed Oct. 7, 2009, which claims benefit of U.S. Provisional Application No. 61/103,741, filed Oct. 8, 2008, the entire contents of each of which are incorporated by reference herein.

FIELD OF THE INVENTION

This invention relates to the field of transdermal delivery, in particular, of hormones.

BACKGROUND OF THE INVENTION

Progestins, or combinations of progestins and estrogens, are used to inhibit ovulation, and to induce other physiological changes in the female reproductive system, and thereby to reduce the risk of pregnancy.

Various dosing regimens have been used to administer such hormones. These include for example, self-administration by oral delivery of a progestin and an estrogen for 21 days, followed by a 7 day "rest" interval, during which the woman typically experiences withdrawal (i.e., menstrual) bleeding. Other dosing regimens can also be used, including dosing regimens that involve longer durations of administration of a progestin and dosing regimens that involve use of low dose hormone during a non-treatment interval.

An important aspect of any effective contraceptive dosing regimen is that the regimen is convenient so as to facilitate compliance and that the doses delivered are effective to prevent or reduce the risk of pregnancy without exposing the woman to unnecessary risks of side effects. Side effects can include hormone-related adverse events and cycle control irregularities, particularly "breakthrough" bleeding.

A transdermal hormone delivery device for administering a progestin and an estrogen via a patch, and a skin permeation enhancer combination for use therein, are disclosed, e.g., in U.S. Pat. No. 7,045,145 and U.S. 20040054901, both of which are incorporated herein by reference as though fully set forth.

SUMMARY OF THE INVENTION

The instant invention provides a dosing regimen for administration of a progestin and, optionally, an estrogen. More specifically, the invention relates to a method of preventing pregnancy, i.e., reducing the risk of pregnancy, in a woman that comprises, during a monthly treatment cycle comprising a treatment interval and a rest interval,
(A) transdermally administering an effective amount of a progestin and, optionally, an estrogen, during a treatment interval of 3 to 4 weeks and
(B) delivering no hormone or transdermally delivering (i) low dose progestin, (ii) low dose estrogen, or (iii) low dose progestin and low dose estrogen during a rest interval that is the balance of the calendar month, if any.

In illustrative embodiments, the invention provides a method of inhibiting conception, i.e., preventing (reducing the risk of) pregnancy, in a woman that comprises, during a monthly treatment cycle consisting of a treatment interval and a rest interval:

(A) applying a transdermal hormone delivery treatment device to the skin of the woman during the treatment interval, e.g., consecutively applying multiple transdermal hormone delivery devices, and
(B) optionally applying a rest interval device during at least a portion of the rest interval, which extends to the end of the calendar month, wherein the rest interval device comprises (i) low dose progestin, (ii) low dose estrogen, (iii) low dose progestin and low dose estrogen, or (iv) no hormone.

In more specific illustrative embodiments, the invention provides a method of inhibiting conception in a woman that comprises consecutively applying, during a monthly treatment cycle:

eight transdermal hormone delivery treatment devices to the skin of the woman during a 28 day treatment interval, each device being applied for ½ week, and each device comprising an effective amount of a combination of an estrogen and a progestin, followed by the rest interval that extends through the balance of the calendar month, if any, or seven transdermal hormone delivery treatment devices to the skin of the woman during a 3½ week treatment interval, each device being applied for ½ week, and each device comprising an effective amount of a combination of an estrogen and a progestin, followed by the rest interval that extends through the balance of the calendar month, or six transdermal hormone delivery treatment devices to the skin of the woman during a 3 week treatment interval, each device being applied for ½ week, and each device comprising an effective amount of a combination of an estrogen and a progestin, followed by the rest interval that extends through the balance of the calendar month, or four transdermal hormone delivery treatment devices to the skin of the woman during a 28 day treatment interval, each device being applied for 7 days, and each device comprising an effective amount of an estrogen and a progestin, followed by the rest interval that extends through the balance of the calendar month, if any, or three transdermal hormone delivery treatment devices to the skin of the woman during a 21 day treatment interval, each device being applied for 7 days, and each device comprising an effective amount of an estrogen and a progestin, followed by the rest interval that extends through the balance of the calendar month.

If a treatment interval is only 3 weeks, such that the rest interval would exceed about 7 days, particularly if the rest interval would exceed 8 days or would exceed 9 days, then a rest interval device comprising low dose hormone would typically be used during all or at least a portion of the rest interval, as illustrated, e.g., by FIG. 1d.

BRIEF DESCRIPTION OF THE FIGURES

FIG. 1a illustrates EE serum concentration levels over 31 days resulting from administration of 7 patches each for 3½ days. FIG. 1b illustrates EE serum concentration levels over 31 days resulting from administration of 7 patches each for 3½ days, followed by administration of a rest interval device (½ patch) for 3½ days. FIG. 1c illustrates EE serum concentration levels over 31 days resulting from administration of 3 patches each for 7 days. FIG. 1d illustrates EE serum concentration levels over 31 days resulting from administration of 3 patches each for 7 days, followed by administration of a rest interval device (½ patch) for 7 days.

DETAILED DESCRIPTION OF THE INVENTION

Figure 1A:
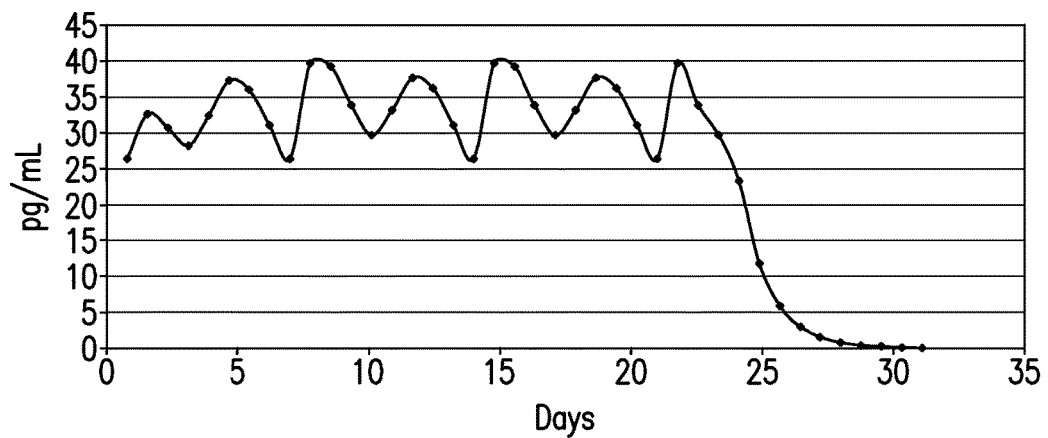
FIGS. 1a, 1b, 1c and 1d (also referred to interchangeably herein as FIG. 1a, FIG. 1b, FIG. 1c and FIG. 1d) illustrate hormone serum concentrations during and after a single treatment cycle comprising a treatment interval of 21 or 24½ days with or without a hormone containing patch in the rest interval. The figures have been drawn to 31 days for illustrative purposes only and do not illustrate hormone serum concentrations during a succeeding treatment cycle.

In accordance with illustrative embodiments of the present invention, during a monthly treatment cycle, in a single treatment interval, multiple, e.g., six, seven, or eight transdermal hormone delivery devices, i.e., "patches," are consecutively applied to the skin of a woman to administer a progestin and, optionally, an estrogen to prevent, i.e., reduce the risk of, pregnancy following sexual intercourse. In illustrative embodiments of the invention, each patch is intended to be worn for ½ week, i.e., for 3 to 4 days, e.g., 3½ days. Thus, the total treatment interval is
  (a) 6 multiplied by ½ week, i.e., 3 weeks,
  (b) 7 multiplied by ½ week, i.e., 3½ weeks, or
  (c) 8 multiplied by ½ week, i.e., 4 weeks.

Each ½ week period is about 3 to about 4 days. For example, a single ½-week device can be worn for 2½ or 3 days of a given week, in which case the other ½-week device would be worn for 4½ or 4 days of that week, respectively, or each device can be worn for 3½ days each.

In accordance with another illustrative embodiment of the invention, during a monthly treatment cycle, in a single treatment interval, three or four transdermal hormone delivery devices, i.e., "patches," are employed to administer a progestin and, optionally, an estrogen to a woman to prevent pregnancy. Each patch is intended to be worn for 1 week. Thus, the total treatment interval is 3 multiplied by 1 week, i.e., 3 weeks, or 4 multiplied by 1 week, i.e., 4 weeks. A one week device can similarly be worn for 6, 6½, 7½, and 8 days, although it is preferable to fix one day per week such that a week is 7 days.

In accordance with another illustrative embodiment of the present invention, during a monthly treatment cycle, in a single treatment interval, four transdermal hormone delivery devices, i.e., "patches," are employed to administer a progestin and, optionally, an estrogen to a woman to prevent conception. Three of the patches are intended to be worn for 1 week each, while the remaining patch is worn for ½ week. Thus, the total treatment interval is 3 multiplied by 1 week, i.e., 3 weeks, plus 1 multiplied by ½ week, i.e., ½ week, which equals 3½ weeks.

In any event, at the end of each treatment interval, there follows a rest interval made up of the days remaining in a given month, if any. So, for example, if the treatment interval is 28 days, as in the case of 4 devices each worn for one week or eight devices each worn for one-half week, and if the treatment interval begins January 1, March 1, May 1, July 1, August 1, October 1, or December 1, then the total treatment cycle is 31 days, including a rest interval of 3 days; if the treatment interval begins April 1, June 1, September, or November 1, then the total treatment cycle is 30 days, including a rest interval of two days; if the treatment interval begins February 1 in a non-leap year, then the total treatment cycle is 28 days, including a rest interval of 0 days; if the treatment interval begins February 1 in a leap year, then the total treatment cycle is 29 days, including a rest interval of 1 day.

Treatment cycles can be repeated successively for as long as desired. This invention contemplates that a woman will generally undergo at least 2 successive treatment cycles before interrupting or altering contraceptive treatment. For example, a woman can undergo 3, 4, 5, 6, or more successive treatment periods. In a typical contraceptive program, a woman will follow such regimen for at least one calendar year.

Treatment intervals need not begin on the first day of a calendar month, but should each begin on a fixed day each month. So, for example, if the treatment interval is 28 days, and if the treatment interval begins January 10, then the last treatment device would be removed on February 7 and the rest interval would comprise February 7, 8, and 9, and the next treatment cycle would being on February 10.

A woman may choose to begin wearing the first patch of the first treatment interval on, or about on, the first day of the woman's period, i.e., on the first day of menstrual bleeding. In this case, the woman can employ a longer or shorter initial treatment interval or initial rest interval, in order to get her on to a schedule that is convenient for her. So, for example, if a woman begins her period on a June 15 and applies the first treatment device that evening, options available to her include, among others:
  (i) going directly to a 28 day treatment interval by consecutively wearing treatment devices for 28 days, i.e., until the evening of July 13, and then having a rest interval until resuming another 28 day treatment interval on July 15;
  (ii) consecutively wearing treatment devices until close to the end of the month, e.g., June 25, 26, 27, 28 or 29, and then having a rest interval until starting a new 28 day treatment interval on July 1;
  (iii) consecutively wearing treatment devices until July 24, 25, 26, 27, 28, 29, or 30, and then having a rest interval until starting a 28 day treatment interval on August 1.

In some embodiments of the invention, there is a minimum treatment interval of 21 days prior to the first rest interval. If the minimum treatment interval is 21 days, then option (ii) in the illustrative example above, would not be available. In any event, after the initial "phase-in" time interval, a 21 to 28 day treatment interval is typically employed, e.g., 21, 24½, or 28 days.

An illustrative regimen for use of seven ½-week devices, starting with application of a first treatment device on the evening of Sunday, Feb. 1, 2009, is illustrated graphically in the following table showing a calendar for February, March, and April, 2009. In these tables, patches are indicated by the superscript or subscript numbers 1 through 7, with superscript values indicating application in the morning and the subscript values indicating application in the evening "RI" indicates the start of the rest interval.

| Illustrative Seven 3-½ Day Patches Regimen | | | | | | |
|---|---|---|---|---|---|---|
| Sun | Mon | Tues | Weds | Thurs | Fri | Sat |
| Treatment Cycle 1 - February 2009 | | | | | | |
| $1_1$ | 2 | 3 | 4 | $5^2$ | 6 | 7 |
| $8_3$ | 9 | 10 | 11 | $12^4$ | 13 | 14 |
| $15_5$ | 16 | 17 | 18 | $19^6$ | 20 | 21 |
| $22_7$ | 23 | 24 | 25 | $26^{RI}$ | 27 | 28 |

Illustrative Seven 3-½ Day Patches Regimen

| Sun | Mon | Tues | Weds | Thurs | Fri | Sat |
|---|---|---|---|---|---|---|
| Treatment Cycle 2 - March 2009 | | | | | | |
| $1_1$ | 2 | 3 | 4 | $5^2$ | 6 | 7 |
| $8_3$ | 9 | 10 | 11 | $12^4$ | 13 | 14 |
| $15_5$ | 16 | 17 | 18 | $19^6$ | 10 | 21 |
| $22_7$ | 23 | 24 | 25 | $26^{RI}$ | 27 | 28 |
| 29 | 30 | 31 | | | | |
| Treatment Cycle 3 - April 2009 | | | | | | |
| | | | $1_1$ | 2 | 3 | 4 |
| $5^2$ | 6 | 7 | $8_3$ | 9 | 10 | 11 |
| $12^4$ | 13 | 14 | $15_5$ | 16 | 17 | 18 |
| $19^6$ | 20 | 21 | $22_7$ | 23 | 24 | 25 |
| $26^{RI}$ | 27 | 28 | 29 | 30 | | |

In an alternative embodiment of the invention, a user applies six 3½ day patches during a treatment interval of 21 days, followed by a rest interval, as illustrated below.

Illustrative Six 3-½ Day Patches Regimen

| Sun | Mon | Tues | Weds | Thurs | Fri | Sat |
|---|---|---|---|---|---|---|
| Treatment Cycle 1 - February 2009 | | | | | | |
| $1_1$ | 2 | 3 | 4 | $5^2$ | 6 | 7 |
| $8_3$ | 9 | 10 | 11 | $12^4$ | 13 | 14 |
| $15_5$ | 16 | 17 | 18 | $19^6$ | 20 | 21 |
| $22_{RI}$ | 23 | 24 | 25 | 26 | 27 | 28 |
| Treatment Cycle 2 - March 2009 | | | | | | |
| $1_1$ | 2 | 3 | 4 | $5^2$ | 6 | 7 |
| $8_3$ | 9 | 10 | 11 | $12^4$ | 13 | 14 |
| $15_5$ | 16 | 17 | 18 | $19^6$ | 10 | 21 |
| $22_{RI}$ | 23 | 24 | 25 | 26 | 27 | 28 |
| 29 | 30 | 31 | | | | |
| Treatment Cycle 3 - April 2009 | | | | | | |
| | | | $1_1$ | 2 | 3 | 4 |
| $5^2$ | 6 | 7 | $8_3$ | 9 | 10 | 11 |
| $12^4$ | 13 | 14 | $15_5$ | 16 | 17 | 18 |
| $19^6$ | 20 | 21 | $22_{RI}$ | 23 | 24 | 25 |
| 26 | 27 | 28 | 29 | 30 | | |

Such regimen results in a rest interval of more than 7 days. Typically, a rest interval would not exceed 7 days. If a regimen is chosen that provides such extended rest interval, it may be advantageous to administer low dose hormone during all or a portion of such rest interval. By "low dose" is meant a dose that is not effective for contraception if used throughout a treatment interval.

In another illustrative embodiment of the invention, a user applies four 7-day patches during a treatment interval of 28 days, followed by a rest interval (if there are any days remaining in the calendar month).

Illustrative Four 7-Day Patches Regimen

| Sun | Mon | Tues | Weds | Thurs | Fri | Sat |
|---|---|---|---|---|---|---|
| Treatment Cycle 1 - February 2009 | | | | | | |
| $1_1$ | 2 | 3 | 4 | 5 | 6 | 7 |
| $8_2$ | 9 | 10 | 11 | 12 | 13 | 14 |
| $15_3$ | 16 | 17 | 18 | 19 | 20 | 21 |
| $22_4$ | 23 | 24 | 25 | 26 | 27 | 28 |
| Treatment Cycle 2 - March 2009 | | | | | | |
| $1_1$ | 2 | 3 | 4 | 5 | 6 | 7 |
| $8_2$ | 9 | 10 | 11 | 12 | 13 | 14 |
| $15_3$ | 16 | 17 | 18 | 19 | 10 | 21 |
| $22_4$ | 23 | 24 | 25 | 26 | 27 | 28 |
| $29_{RI}$ | 30 | 31 | | | | |
| Treatment Cycle 3 - April 2009 | | | | | | |
| | | | $1_1$ | 2 | 3 | 4 |
| 5 | 6 | 7 | $8_2$ | 9 | 10 | 11 |
| 12 | 13 | 14 | $15_3$ | 16 | 17 | 18 |
| 19 | 20 | 21 | $22_4$ | 23 | 24 | 25 |
| 26 | 27 | 28 | $29_{RI}$ | 30 | | |

It will be appreciated that in each of the above illustrations, the first day of each treatment cycle, i.e., the first day of application of a new device, is designated as Day 1. It could have been designated Day 0 (as in FIGS. 1a, 1b, 1c and 1d, discussed below) in which case, all other day numbers would be reduced by one. It will further be appreciated that the first application in this illustration is made on the afternoon/evening of Day 1, shown here as a Sunday, but that the first application can also be made on a Sunday morning or in the morning, afternoon, or evening of any other day of the week.

It should also be appreciated that while the above illustrations use 3½ days as a ½ week interval, it is also possible in accordance with this invention to wear one patch for 2½ to 4½ days, e.g., 3-4 days per week, and another patch for the balance of the week, so long as two successive ½ week periods total seven or about seven days. Preferably, at least one day per week is fixed, e.g., each Sunday either a new device is applied or a rest interval begins. This is illustrated in the following table for eight ½-Week patches.

Illustrative Eight ½-Week Patches Regimen

| Sun | Mon | Tues | Weds | Thurs | Fri | Sat |
|---|---|---|---|---|---|---|
| Treatment Cycle 1 - February 2009 | | | | | | |
| $1_1$ | 2 | 3 | 4 | $5^2$ | 6 | 7 |
| $8^3$ | 9 | 10 | $11_4$ | 12 | 13 | 14 |
| $15_5$ | 16 | 17 | 18 | $19_6$ | 20 | 21 |
| $22_7$ | 23 | 24 | $25^8$ | 26 | 27 | 28 |
| Treatment Cycle 2 - March 2009 | | | | | | |
| $1_1$ | 2 | 3 | $4^2$ | 5 | 6 | 7 |
| $8_3$ | 9 | 10 | 11 | $12_4$ | 13 | 14 |
| $15^5$ | 16 | 17 | $18_6$ | 19 | 20 | 21 |
| $22_7$ | 23 | 24 | $25^8$ | 26 | 27 | 28 |
| $29_{RI}$ | 30 | 31 | | | | |
| Treatment Cycle 3 - April 2009 | | | | | | |
| | | | $1_1$ | 2 | 3 | 4 |
| $5_2$ | 6 | 7 | $8_3$ | 9 | 10 | 11 |
| $12_4$ | 13 | 14 | 15 | $16_5$ | 17 | 18 |
| $19_6$ | 20 | 21 | 22 | 23 | $24^7$ | 25 |
| $26^8$ | 27 | 28 | $29_{RI}$ | 30 | | |

In other embodiments, each ½ week is fixed at 3½ days.

In embodiments of the invention, only a progestin is administered during treatment intervals. In other embodiments, the progestin is administered in combination with an estrogen during treatment intervals, for all or a portion of each treatment interval. In either case, a progestin or an estrogen or both can but is not necessarily administered during all or a portion of the rest interval, as described below.

The amount of hormone in each treatment device, e.g., each 3½ day patch or 7 day patch, can be varied from patch to patch, or week to week, to provide a multiphasic treatment regimen. For example, the amounts of hormone can be varied so as to provide a triphasic delivery regimen such as, e.g., the triphasic oral contraceptive disclosed in U.S. Pat. No. 6,214,815 (Ortho-McNeil). Either or both of the progestin and the estrogen can be varied (or maintained) independently of each other. Alternatively, the amount of the progestin and of the estrogen can be the same in all patches used in a given treatment cycle or in all treatment cycles.

It is desirable that each treatment device result in an average progestin serum concentration level equivalent to at least about 750 pg/ml of levonorgestrel during the entire treatment interval. In some embodiments, the average progestin serum concentration level is equivalent to at least about 500 pg/ml of levonorgestrel during week 1 of the treatment interval and/or is at least about 750 pg/ml during week 2 and week 3 of each treatment interval, it being understood, however, that such levels may not be achieved during the entire first treatment cycle. In particular, for example, such levels may not be achieved during the first week of the first treatment cycle.

In addition, serum concentrations of a progestin, as well as of an estrogen, can vary from patient to patient. Thus, when considering average serum concentrations achieved during treatment intervals, it is useful to refer to a population of subjects, e.g., 10 or more, 25 or more, 50 or more, 75 or more, or 100 or more. Thus, the concentration values, and peak-trough relationships, expressed herein may be achieved in a population of subjects but not necessarily in every subject within a given population.

The amount of estrogen delivered during each treatment interval can be an amount that results in serum concentration levels equivalent to about 5 to about 80, e.g., about 15 to about 65, pg/ml of ethinyl estradiol during the entire treatment interval, or about 20 to about 30 pg/ml. Serum concentration levels that average about 20 to about 30 pg/ml ethinyl estradiol equivalent can be achieved during week 2 and week 3 of each treatment interval.

In an illustrative embodiment of the invention, low (or lower) dose hormone(s) can be delivered during all or a part of the rest interval. The amount of hormone delivered during the rest interval is no more than about 80%, e.g., about 20% to about 80%, of the amount delivered during the treatment interval. For example, the amount of hormone(s) delivered during the rest interval can be about ¾, about ⅔, about ½, about ⅓, or about ¼ of the amount delivered during an equivalent amount of time during the treatment interval. Such amount may attenuate, i.e., lessen the severity of, symptoms of menstruation, which can include excessive vaginal bleeding, mood changes, headaches, dysmenorrhea and other symptoms associated with hormone withdrawal, especially sudden hormone withdrawal, or otherwise.

Such rest interval patch, or rest interval device, can conveniently be made in the same manner as the treatment device but with a reduced amount of hormone(s). The amount of hormone(s) can be reduced, for example, by reducing the size of the patch. For example, if a treatment patch has a surface area of 20 cm² and it is desired to deliver 50% of the hormones during the rest interval, then the rest interval device can be the same as the treatment interval device but reduced in size to have a surface area of 10 cm². Such rest interval device could be referred to as a "half patch." Similarly, one could administer a "quarter patch" to deliver 25% of the hormones, or a patch of any other fraction of the size of the treatment patch. Alternatively, the size (surface area) of the rest interval device can be the same as the size of the treatment device, in which case it would be loaded with reduced amounts of hormones and/or enhancers.

The rest interval device can be worn for any part or the whole of the rest interval. So, for example, a half patch can be worn for the full rest interval.

FIGS. 1a, 1b, 1c and 1d show illustrative hormone serum concentration levels over 31 days. In accordance with the practice of this invention, of course, a fresh device would be applied sooner during months with 28, 29, or 30 days.

As illustrated in FIGS. 1a, 1b, 1c and 1d, patches can be designed so as to deliver varying amounts of hormone(s) during the period of wear of each patch, such that there is a peak serum concentration level that occurs after the patch is applied and a trough serum concentration level that occurs at the time the patch is removed. This characteristic can be usefully employed to deliver an amount of a progestin or an estrogen, or both, during the rest interval that declines as the end of the rest interval approaches such that the amount of hormone delivered by the end of the rest interval is decreased relative to peak levels during wear of the rest interval device and, in some embodiments, relative to serum concentration levels on the day that the rest interval device is applied. Such device can be referred to as a descending dose device.

Use of such rest interval device can have several advantages. In one embodiment, the rest interval device is a placebo and is used as a matter of convenience, e.g., so that the woman stays in the habit of removing and applying a patch every 3-12 days or every 7 days. In another embodiment, low dose hormone is delivered such that the woman experiences menstruation but with attenuated symptoms. In such embodiment, also, hormone serum concentration levels are adjusted gradually rather than "all or nothing".

A 3½ day patch can be smaller than a 7 day patch therefore making it less noticeable to the wearer and persons around her. The adhesiveness requirements are also eased because the patch is smaller and because it doesn't need to stay attached for a full week. If a 3½ day patch does become dislodged, there will only be a short period of time before the next patch is due to be applied. A 3½ day patch can allow for a pharmacokinetic (PK) profile having peaks and troughs during each wear period, i.e., during each 3½ day period of treatment, but such peaks and troughs can be smoother relative to a 7 day patch. So, for example, peak hormone serum concentrations during the period of time in which a single treatment device (other than the first device) is worn can be at least about 1.1 times trough levels, or at least about 1.25 times the trough levels, but also can be no more than about twice the trough levels, or no more than about 1.8 times the trough levels, or no more than about 1.5 times the trough levels. FIGS. 1a, 1b, 1c and 1d illustrate such peak-trough PK profiles. Such PK profile can be achieved during an entire treatment interval or during at least a single wear interval, e.g., the third week, the second half of the second or third weeks, or at least 2 weeks, e.g., the second and third weeks, of each treatment interval.

Any transdermal hormone delivery device that delivers a progestin and, optionally, an estrogen, in amounts effective to effect contraception, i.e., to prevent pregnancy, can be used in the practice of the invention. "Preventing pregnancy" does not necessarily mean that such devices are 100% effective in preventing pregnancy in all cases but such devices can have, at least, approximately the same contraceptive efficacy as currently available oral contraceptives. A transdermal hormone delivery device for preventing pregnancy that delivers 17-deacetyl norgestimate and ethinyl estradiol is disclosed in U.S. Pat. No. 5,876,746 (Cygnus) and is marketed as Ortho Evra(r) (norelgestromin/ethinyl estradiol transdermal system). As shown in the prescribing information, Ortho Evra provides a more or less "flat" delivery, i.e., no or only a slight peak-trough PK profile for each period of wear of a single patch.

The invention also comprises a kit comprising multiple patches each intended to be worn for ½ week (2½ to 4½ days) or 1 week (6-8 days). For example, such kit may comprise seven ½ week treatment devices, or some multiple of 7, e.g., 14, 21, 28, 35, or 42 treatment devices. Or, for example, such kit may comprise six ½ week treatment devices, or some multiple of 6, e.g., 12, 18, 24, 30, 36, 42, 48, 54, 60, 66, or 72 treatment devices. Or, for example, such kit may comprise three 7 day treatment devices, or some multiple of 3, e.g., 3, 6, 9, 12, 15, 18, 21, 24, 27, 30, 33, or 36 treatment devices. Each kit can also comprise a mix of ½ week and one week devices. For example, a kit may comprise three 7 day treatment devices, or some multiple of 3, e.g., 3, 6, 9, 12, 15, 18, 21, 24, 27, 30, 33, or 36 treatment devices, and one ½ week treatment device for every three one week devices. In each case, the kit would include instructions for use of the devices in accordance with the method of the invention.

Such kit can also comprise rest interval devices, which can be placebos (i.e., no hormone) or low dose hormone devices, as discussed above. For example, a kit for a seven patches/treatment cycle regimen can comprise forty-two ½ week treatment devices and six rest interval devices; a kit for a six patches/treatment cycle regimen can comprise seventy-two ½ week treatment device and twelve rest interval devices; a kit for a 3 patches/treatment cycle regimen can comprise nine 7 day treatment devices and three rest interval devices; etc.

Such rest interval devices can be clearly indicated as rest interval devices, directly or on individual patch packaging, such as by size, color, shape, or markings, to avoid confusion with treatment devices. If a multiphasic hormone delivery profile is desired, then each treatment device can be marked, directly or on individual patch packaging, to minimize the risk that a user will apply patches out of order.

FIGS. 1a, 1b, 1c and 1d illustrate projected serum concentration levels of ethinyl estradiol (EE) resulting from administration of patches such as described in U.S. Pat. No. 7,045,145 and U.S. 20040054901 and hereinbelow.

Figure 1B:
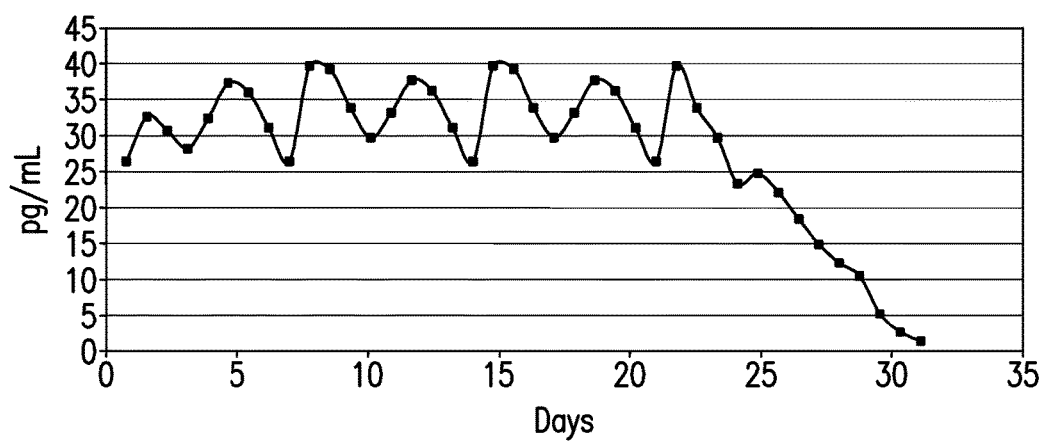
Figure 1C:
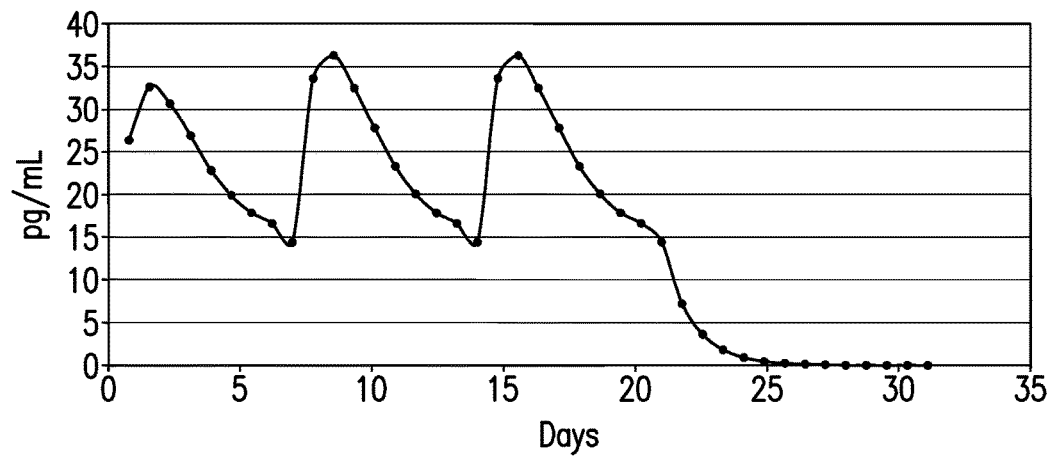
Figure 1D:
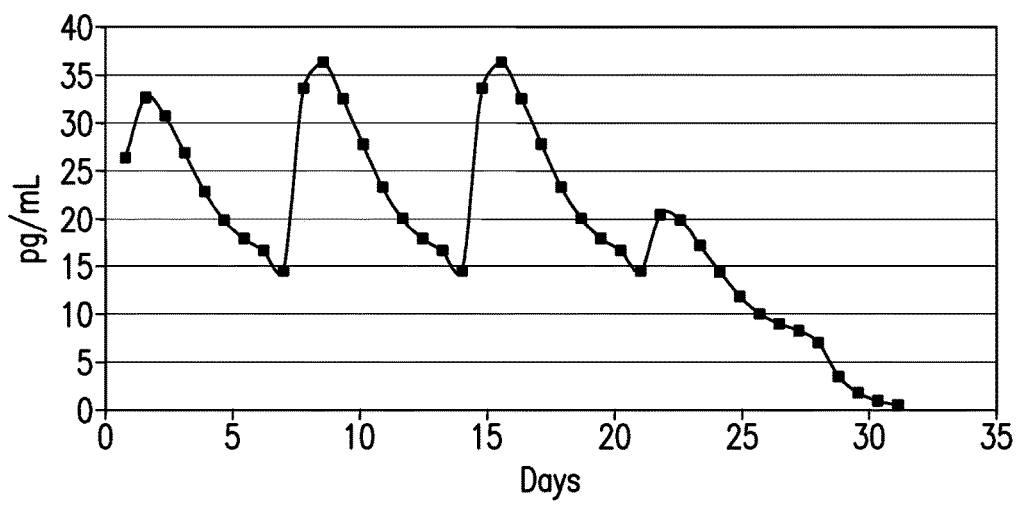

The data in FIGS. 1a, 1b, 1c and 1d are illustrative and do not show the effect of applying a new patch on Day 29. The data are projections calculated on the basis of actual human cadaver skin flux data obtained using a device loaded with a polymeric matrix comprising LNG and EE, substantially as described below, and having a skin contact area of approximately 9.4 cm$^2$. The projections are calculated using an approximate in vivo clearance rate for EE. FIGS. 1a and 1b show EE levels on each of Days 1 through 28, with a first 3½ day patch being applied on Day 0 and subsequent patches being applied on Days 4, 7, 11, 14, 18, and 21. FIGS. 1c and 1d show EE levels on each of Days 1 through 28, with a first 7 day patch being applied on Day 0 and subsequent patches being applied on Days 7 and 14. FIGS. 1b and 1d show the effects of administering a rest interval patch on Days 24-28, said rest interval device being ½ the size of, but otherwise identical to, the treatment patch.

A similar pattern of peaks/troughs can be obtained with progestins, e.g., LNG.

Note that because these data are projected from skin flux data, actual results will vary, depending, e.g., upon the skin surface area of the patch employed, the concentration of hormone(s), and the efficacy of the skin permeation enhancer.

Figure 2:
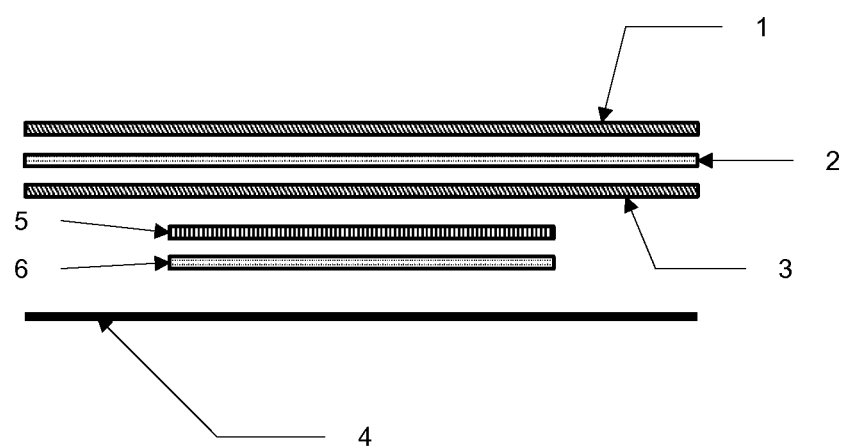
FIG. 2 illustrates an exploded cross-section of an illustrative dermal delivery system of the invention.

An illustrative device that can be used in the practice of the instant invention is illustrated in FIG. 2.

With reference to FIG. 2, this illustrative device comprises 4 layers. One is the AI layer (6). The second is a release liner (4). The third is an internal backing layer (5). The fourth is an overlay, which in this illustrative device, itself comprises three component layers (1, 2, 3), referred to herein below as, respectively, a PSA layer (3), an intermediate layer (2), and an overlay covering or overlay coating (1). The overlay can also be described as comprising a PSA layer (3) and an overlay covering (1, 2). In any event, a feature of this device is formation of a seal between the PSA layer (3) of the overlay (1, 2, 3) and the release liner (4). The AI layer Layer 6 comprises the AI and carriers comprising skin permeation enhancers, a humectant/plasticizer, and a PSA matrix. The AI comprise a progestin, e.g., levonorgestrel, and an estrogen, e.g., ethinyl estradiol or 17-β estradiol.

Skin Permeation Enhancers: A combination of skin permeation enhancing agents is employed that comprises a mixture of (1) a pharmaceutically acceptable organic solvent, such as dimethyl sulfoxide (DMSO), (2) a fatty (C8-C20) alcohol ester of a hydroxy acid, such as lauryl lactate, (3) a lower (C1-C4) alkyl ester of a hydroxy acid, e.g., ethyl lactate, and (4) a C6-C18 fatty acid, such as capric acid. In specific embodiments, the fatty alcohol ester of lactic acid is lauryl lactate and the lower alkyl ester of lactic acid is ethyl lactate. A medium- to long-chain fatty acid in the skin permeation enhancer formulation can be employed among the skin permeation enhancers. Capric acid has been used but other C6-C18 saturated or unsaturated fatty acids include but are not limited to caproic acid, caprytic acid, lauric acid and myristic acid.

In a particular such embodiment, the pharmaceutically acceptable organic solvent is DMSO. Other organic solvents include but are not limited to C1-C8 branched or unbranched alcohols, such as ethanol, propanol, isopropanol, butanol, isobutanol, and the like, as well as azone (laurocapram: 1-dodecylhexahydro-2H-azepin-2-one) and methylsulfonylmethane.

The fatty alcohol ester of a hydroxy acid can be a fatty alcohol ester of lactic acid, such as lauryl lactate. However, other hydroxy acids and fatty alcohols may be utilized. Alternative hydroxy acids include but are not limited to alpha-hydroxy acids such as glycolic acid, tartaric acid, citric acid, malic acid and mandelic acid, as well as the beta-hydroxy acid, salicylic acid. Alternative fatty alcohols include any C8-C20 saturated or unsaturated fatty alcohols, such as myristyl, palmityl or oleyl alcohols, to name a few.

The lower alkyl ester of hydroxy acid can also utilize lactic acid, and can be, e.g., ethyl lactate. However, other hydroxy acids, such as glycolic acid, tartaric acid, citric acid, malic acid, mandelic acid and salicylic acid, may also be utilized. In addition isopropylmyristic acid (IPM) may be used as a substitute for the lower alkyl ester of hydroxy acid.

Hormones: LNG is a potent progestin on a weight-dose basis, which is an important factor since progestins often exhibit a much lesser degree of transdermal absorption than do estrogens. Other progestins that could be used in part or total are norgestrel, norgestimate, desogestrel, gestodene, norethindrone, nore-thynodrel, hydrogesterone, ethynodiol dicetate, hydroxyprogesterone caproate, medroxyprogesterone acetate, norethindrone acetate, progesterone, megestrol acetate, gestogen and certain others which are biocompatible and absorbable transdermally. These include biocompatible derivatives of progestins that are transdermally absorbed, some of which, advantageously, are bioconvertible after transdermal absorption to the original progestin. The progestin and other hormones selected preferably have high compatibility with each other.

For combinations of progestin with estrogen, the synthetic hormone EE is particularly suitable, although natural estrogen or other analogs can be used. This hormone may be transdermally delivered in conjunction with the particularly suitable progestin, levonorgestrel, at desirable daily rates for both hormones. EE and LNG are compatible and can be dispersed in the adhesive polymer formulation.

Derivatives of 17 β-estradiol that are biocompatible, capable of being absorbed transdermally and preferably bioconvertible to 17 β-estradiol may also be used, if the amount of absorption meets the required daily dose of the estrogen component and if the hormone components are compatible. Such derivatives of estradiol include esters, either mono- or di-esters. The monoesters can be either 3- or 17-esters. The estradiol esters can be, illustratively speaking, estradiol-3, 17-diacetate; estradiol-3-acetate; estradiol 17-acetate; estradiol-3, 17-divalerate; estradiol-3-valerate; estradiol-17-valerate; 3-mono-, 17-mono- and 3,17-dipivilate esters; 3-mono-, 17-mono- and 3,17-dipropionate esters; 3-mono-, 17-mono- and 3,17-dicyclo pentyl-propionate esters; corresponding cypionate, heptanoate, benzoate and the like esters; ethinyl estradiol; estrone; and other estrogenic steroids and derivatives thereof that are transdermally absorbable.

Combinations of the above with estradiol itself (for example, a combination of estradiol and estradiol-17-valerate or further a combination of estradiol-17-valerate and estradiol-3, 17-divalerate) can be used with beneficial results. For example, 15-80% of each compound based on the total weight of the estrogenic steroid component can be used to obtain the desired result. Other combinations can also be used to obtain desired absorption and levels of 17 β-estradiol in the body of the subject being treated.

It will be appreciated that the hormones may be employed not only in the form of the pure chemical compounds, but also in a mixture with other pharmaceuticals that may be transdermally applied or with other ingredients which are not incompatible with the desired objective as listed above. Thus, simple pharmacologically acceptable derivatives of the hormones such as ethers, esters, amides, acetals, salts and the like, if appropriate, may be used. In some cases, such derivatives may be preferred. The progestin compound and the estrogenic steroid are ordinarily dispersed or dissolved concurrently in fabricating the hormone-containing adhesive polymer matrix or they may be dispersed or dissolved separately.

Polymers Used as Active Patch Components: The AI-containing layer can be a polymer matrix comprising the pharmaceutically or cosmetically active ingredient. The polymer can be a PSA to form a biologically acceptable adhesive polymer matrix, preferably capable of forming thin films or coatings through which the AI can pass at a controlled rate. Suitable polymers are biologically and pharmaceutically compatible, nonallergenic, insoluble in and compatible with body fluids or tissues with which the device is contacted. The use of water soluble polymers is generally less preferred since dissolution or erosion of the matrix would affect the release rate of the AI as well as the capability of the dosage unit to remain in place on the skin. So, in certain embodiments, the polymer is non-water soluble.

Preferably, polymers used to form a polymer matrix in the AI-containing layer have glass transition temperatures below room temperature. The polymers are preferably non-crystalline but may have some crystallinity if necessary for the development of other desired properties. Cross-linking monomeric units or sites can be incorporated into such polymers. For example, cross-linking monomers that can be incorporated into polyacrylate polymers include polymethacrylic esters of polyols such as butylene diacrylate and dimethacrylate, trimethylol propane trimethacrylate and the like. Other monomers that provide such sites include allyl acrylate, allyl methacrylate, diallyl maleate and the like.

In certain transdermal drug delivery devices, there is a a permeable or rupturable barrier, rate controlling membrane, or the like interposed between the AI-containing material and the release liner such that when the release liner is removed, said barrier remains in place. The purpose of such barrier can be, e.g., to prevent the AI-containing material from flowing out of the device or to control the rate of absorption by the skin. In the device used to generate the data illustrated in FIGS. 1a, 1b, 1c and 1d, there is no need for a layer between the release liner and the AI layer because the polymer matrix is adhered to the remaining layers of the device and does not readily flow and because the matrix is designed to deliver adequate drug across the skin without a need to restrict the flow rate. Thus, the polymer matrix is adhered directly to the release liner and, upon administration to the skin, the polymer matrix is adhered directly to the skin across the entire surface area of the AI layer exposed by removal of the release liner.

A useful adhesive polymer formulation comprises a polyacrylate adhesive polymer of the general formula (I):

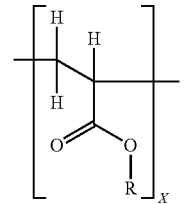

wherein "X" represents the number of repeating units sufficient to provide the desired properties in the adhesive polymer and R is H or a lower (C1-C10) alkyl, such as ethyl, butyl, 2-ethylhexyl, octyl, decyl and the like. More specifically, it is preferred that the adhesive polymer matrix comprises a polyacrylate adhesive copolymer having a 2-ethylhexyl acrylate monomer and approximately 50-60% w/w of vinyl acetate as a co-monomer. An example of a suitable polyacrylate adhesive copolymer for use in the present invention includes, but is not limited to, that sold under the tradename of Duro Tak 87-4098 by National Starch and Chemical Co., Bridgewater, N.J., which comprises a certain percentage of vinyl acetate co-monomer.

Humectant/plasticizer: Preferably, a plasticizer/humectant is dispersed within the adhesive polymer formulation. Incorporation of a humectant in the formulation allows the dosage unit to absorb moisture from the surface of skin which in turn helps to reduce skin irritation and to prevent the adhesive polymer matrix of the delivery system from failing. The plasticizer/humectant may be a conventional plasticizer used in the pharmaceutical industry, for example, polyvinyl pyrrolidone (PVP). In particular, PVP/vinyl acetate (PVP/VA) co-polymers, such as those having a molecular weight of from about 50,000, are suitable for use in the present invention. The PVP/VA acts as both a plasticizer, acting to control the rigidity of the polymer matrix, as well as a humectant, acting to regulate moisture content of the matrix. The PVP/VA can be, for example, PVP/VA S-630 which is a 60:40 PVP:VA co-polymer that has a molecular weight of 51,000 and a glass transition temperature of 110 C. The amount of humectant/plasticizer is directly related to the duration of adhesion of the overlay. The PVP/vinyl acetate can be PVP/VA S-630 supplied by International Specialty Products, Inc. (ISP) of Wayne, N.J., wherein the PVP and the vinyl acetate are each present in approximately equal weight percent.

The shape of the device of the invention is not critical. For example, it can be circular, i.e., a disc, or it can be polygonal, e.g., rectangular, or elliptical. The surface area of the AI layer generally should not exceed about 60 cm$^2$ in area. Preferably, it will be about 5 to 50 cm$^2$, more preferably, about 8 to about 40 cm$^2$. Most preferably, the discs will be about 10 to about 20 cm$^2$. A disc of 15 cm$^2$ may be preferred because it is relatively small but can be capable of dispersing high levels of hormones.

Thus, an illustrative hormone-comprising polymer matrix useful for delivering an effective amount of a progestin and of an estrogen in amounts effective to prevent pregnancy in accordance with the method of the invention comprises a polyacrylate adhesive copolymer with about 3% to about 60% w/w vinyl acetate and, on a weight percentage basis of the adhesive polymer matrix:
   a) from about 15% to about 35% of PVP/VA;
   b) from about 10% to about 30% percent of a combination of skin permeation enhancing agents which is a mixture comprising from about 4% to about 12% DMSO, from about 4.2% to about 12.6% lauryl lactate, from about 0.7% to about 2.3% ethyl lactate, and from about 3% to about 9% capric acid; and
   c) from about _0.6% to about 1.2% LNG and EE, e.g., about 0.87% LNG and about 0.77% EE.

The Internal Backing Layer

An internal backing layer can be made of any suitable material that is impermeable or substantially impermeable to the AI and to excipients of the adhesive polymer matrix. The internal backing layer serves as a protective cover for the AI layer and provides a support function. The backing layer can be formed so that it is essentially the same size as the hormone-containing adhesive polymer matrix or it can be of larger dimension so that it can extend beyond the edges of the AI-containing patch outwardly. The backing layer can be any appropriate thickness that will provide the desired protective and support functions. A suitable thickness is from about 10 to about 300 microns. More specifically, the thickness is less than about 150 microns, yet more specifically, it is less than about 100 microns, and most specifically, the thickness is less than about 50 microns.

Examples of materials suitable for making the internal backing layer are films of polypropylene, polyesters such as poly(ethylene terephthalate), metal foils, metal foil laminates of such suitable polymer films, and the like. Polyester films, such as Mylar® (DuPont Teijin) and Scotchpak® 9732 (3M Company), are particularly suitable for use in the present invention.

The Release Liner

The surface area of the release liner is greater than that of the AI layer. This can be seen in FIG. 2, where the diameter (in the case of a round device) or width and length (in the case of a polygonal device) of Layer 3 is greater than that of Layers 5 and 6, such that it extends beyond the AI layer in some or all directions.

The release liner is made of any material (1) that is impermeable or substantially impermeable to the components of the AI layer, (2) to which the PSA in the overlay will adhere, as discussed further hereinbelow, and (3) that is readily removable by peeling from the AI layer and overlay PSA just prior to applying to the skin.

The release liner can have the same dimensions as the overlay, discussed below, or it can extend totally or partially beyond the edge of the patch. In one embodiment, the release liner extends partially beyond the overlay so as to form "tabs" of release liner material that extend beyond the edges of the overlay for easy separation of the release liner from the rest of the system.

It can comprise a fluorinated or siliconized polyester film or another fluorinated or siliconized polymer such as a polyacrylonitrile copolymer, or a foil lined with a siliconized or fluorinated polymer. The release liner is preferably not polystyrene because it has been shown that polystyrene will absorb DMSO. A preferred material for the release liner when the layer 4a of the overlay comprises a PIB PSA is a Scotchpak® liner (3M Company), such as Scotchpak® 1022 or Scotchpak® 9744 fluorinated polyester release liners.

The Overlay

The overlay comprises a PSA in which the solubility of the volatile components is less, preferably significantly less, than the solubility of those same components in the AI matrix. So, e.g., when the volatile component is DMSO or ethyl lactate, a PIB PSA may be chosen. With reference to FIG. 2, the PIB PSA layer is Layer 3. Generally, such PIB PSA comprises a mix of a low to medium molecular weight and a high molecular weight PIB, a plasticizer such as polybutene, and a hydrocolloid such as a cross-linked polyvinylpyrrolidine. Useful PIBs include, e.g., Oppanol® PIBs (BASF), which have average molecular weights of between 40,000 and 4,000,000.

A useful PIB PSA comprises crospovidone such as Kollidon® CLM crospovidone (BASF) (e.g., 5-45 wt %, preferably 15-30 wt %, and more preferably 20-25 wt %); a low viscosity PIB such as Oppanol® B12 (molecular weight: 51000, viscosity at 150 C: 150 Pascal-seconds) (e.g., 10-60 wt %, preferably 30-50 wt %); a high viscosity PIB such as Oppanol® B100 (viscosity: approximately 1100 Pascal-seconds) (e.g., 2-15 wt %, preferably 5-15 wt %); a polybutene such as Indopol® 1900 (Innovene LLC) (molecular weight: 2500, viscosity at 100 C: 3900-4200 centistokes) (e.g., 10-60 wt %, preferably 20-40 wt %); and a mineral oil (0-20 wt %). For example, an illustrative formulation comprises about 20 wt % crospovidone, about 40 wt % of a low viscosity PIB, about 8 wt % of a high viscosity PIB and about 32 wt % of polybutene. (The term, "about," as used in this specification, means plus or minus 10%. By "low viscosity" is meant less than about 300 Pascal-seconds and by "high viscosity" is meant more than about 800 Pascal-seconds, when the viscosity is measured at 150 C.) Cross-linking of the PVP is useful because such cross-linked polymers tend to be water-swellable but water insoluble. Such PIB PSA can provide good wear stability, e.g., attachment under normal living conditions for at least 7 days.

Other rubber-based polymers that can be used in place of PIB PSA in the overlay include silicone-based PSAs, such as BIO-PSA® (Dow Corning); copolymers and terpolymers of styrene/butadiene/styrene, styrene/isoprene/styrene, and styrene-ethylene/butylenes-styrene, such as Kraton D styrene/ butadiene and Kraton G styrene-ethylene/butylene-styrene or styrene-ethylene/propylene-styrene. Isoprene rubbers, such as Kraton IR linear polyisoprene homopolymers, can also be used.

As shown in FIG. 2, and like the release liner, the overlay can extend beyond the perimeter of the AI layer in all directions, typically by a margin of about 0.1 to about 1.5 cm, more specifically about 0.3 to about 1.2 cm, and yet more specifically about 0.8 cm beyond the perimeter of the AI layer.

The overlay, if it comprises a PSA layer, improves adherence to the skin by supplementing the adhesion provided by the PSA in the AI layer, if present, or, in the case of an AI layer that does not comprise a PSA, it provides adherence to the skin.

In addition, the overlay adheres to the release liner around the perimeter of both layers, thereby sealing in the components of the AI layer. By properly selecting the materials that comprise the overlay and the release liner, this seal between them prevents, or substantially prevents, escape of the volatile component in the AI layer but still allows the release liner to be peeled away easily by the user prior to topical application.

The seal is formed in situ by mechanically pressing together the edges of the overlay that extend beyond the perimeter of the AI layer and the edges of the release liner that extend beyond the perimeter of the AI layer. When the first overlay layer is a PIB PSA and the release liner is a fluorinated or siliconized polyester film, a suitable seal can be made by applying pressure. The amount of pressure required to form such seal is not critical. Finger pressure is adequate. Of course, in an illustrative embodiment of the invention, it is desirable that the seal can be broken by peeling the release liner from the rest of the system by hand just prior to application to the skin.

The seal between the overlay PSA and the release liner prevents, or substantially prevents, loss of the components of the AI layer through the seal between these two layers such as during storage of the system. The seal is preferably "tight" to the internal backing layer and the AI layer such that there is minimal or no seepage of the polymer matrix into spaces between the overlay and the release liner or between the overlay and the internal backing layer or the AI layer.

The overlay can also comprise a covering (1) that does not comprise a PSA, i.e., that comprises a non-PSA layer, such that the surface of the overlay that is exposed to fingers, clothing and ambient dirt or dust is non-tacky, is flexible or malleable so as to flex with skin and muscle movements, is of an unnoticeable or attractive color and texture, and permits moisture from the skin to pass through the device owing to its being porous or otherwise permeable to water.

Thus, it may be desirable to utilize a multi-layered overlay comprising a first layer of a PSA in which the volatile component is insoluble, covered with an intermediate layer and an overlay covering having the properties described above. Such illustrative overlay is illustrated in FIG. 2 as Layers 1, 2, and 3.

While a PIB PSA is useful for containing DMSO or ethyl lactate, or both, in the AI layer, the PIB PSA may flow through most overlay coverings having the properties described above. Such flow of the PIB PSA can cause the device to become tacky and discolored. Therefore, it may be desirable to use an overlay covering that itself comprises two layers, one of which is a polymeric layer interposed between the PIB PSA (an intermediate layer) and a backing layer. Such intermediate layer can be a polyacrylate PSA as described above, because such PSA will substantially prevent flow of the PIB PSA into and through the overlay covering but will substantially not itself migrate into or through the overlay covering.

The overlay is a laminate that comprises three layers: a PIB PSA layer (3, in FIG. 2); an intermediate layer that comprises a material that does not permit flow of the PIB PSA but that does permit passage of moisture (2, in FIG. 2); and an overlay covering (or backing layer) that is non-tacky, attractive, flexible, and moisture permeable (1, in FIG. 2).

Materials useful in the intermediate layer include, e.g., polyacrylates, polyurethanes, plasticized polyvinyl chlorides, and copolymers of polyethylene and ethyl vinyl acetate. Rubber-based polymers that are of very high molecular weight, e.g., at least about 150,000 Daltons can also be used, as can rubber-based polymers that can be crosslinked Examples include the Kraton D styrene/butadiene, Kraton G styrene-ethylene/butylene-styrene or styrene-ethylene/propylene-styrene and Kraton IR linear polyisoprene homopolymers Butyl rubbers and silicone rubbers, which are cross-linkable, can also be used. The intermediate layer can comprise a PSA that binds the first overlay layer as well as the overlay covering. High molecular weight, cross-linked polymers are preferred. Preferably, such PSA is a polyacrylate such as is described above with reference to the AI layer.

Materials used in the overlay covering are not PSAs. They include, for example, a polyurethane film, foam or spun bonded structure, a polyolefin foam, a PVC foam or a woven or non-woven fabric. Illustrative wovens include KOB 051, 053 and 055 woven polyesters (Karl Otto Braun.) Illustrative non-woven fabrics include polyesters. An illustrative polyurethane material is CoTran™ 9700 melt-blown polyurethane nonwoven backing (3M), which can be colored in skin tones. Suitable materials are described, e.g., as backing layers in U.S. Pat. No. 6,660,295.

If the overlay covering is not porous, then it can be used without an intermediate layer. However, if the overlay covering is not porous, adhesion problems can result from a build up of moisture in the skin/PIB PSA interface. Use of a solid material, i.e., one that is not porous, but that is otherwise permeable to water, such as a thin, e.g., 1 mil (i.e., 0.001 inch), polyurethane film, can be used. However, a porous material such as a foam or fabric will, in general, better retain its shape and provide good adhesion.

The present invention is not limited to the embodiments described and exemplified above, but is capable of variation and modification within the scope of the appended claims. Published patent applications and patents referenced in this specification are incorporated herein by reference as though fully set forth.

The invention claimed is:

1. A method of preventing pregnancy in a woman that comprises, during a treatment cycle based on a calendar month:
   (A) transdermally administering a contraceptively effective amount of a progestin and an estrogen during a three-week or four-week treatment interval by successive weekly applications of three or four transdermal hormone delivery treatment interval devices, one for each week of the treatment interval; and
   (B) transdermally administering low dose progestin and low dose estrogen throughout a rest interval that is the balance of the calendar month by application of a low dose transdermal hormone delivery device during the rest interval, wherein the rest interval device delivers between 25% and 75% of the amount of progestin and between 25% and 75% of the amount of estrogen as delivered by each treatment interval device;

whereby the woman experiences menstruation during the rest interval;

wherein the estrogen is selected from one or more of: estradiol-3, 17-diacetate; estradiol-3-acetate; estradiol 17-acetate; estradiol-3, 17-divalerate; estradiol-3-valerate; estradiol-17-valerate, 3-mono-, 17-mono- and 3, 17-dipivilate esters; 3-mono-, 17-mono- and 3, 17-dipropionate esters; 3-mono-, 17-mono- and 3, 17-dicyclo pentyl-propionate esters; 3-mono-, 17-mono- and 3, 17-dicyprionate esters; 3-mono-, 17-mono- and 3, 17-diheptanoate esters; 3-mono-, 17-mono- and 3, 17-dibenzoate esters; ethinyl estradiol; and estrone; and the progestin is selected from one or more of: levonorgestrel; norgestrel; norgestimate; 17-deacetyl norgestimate; desogestrel; gestodene; norethindrone; norethynodrel; hydrogesterone; ethynodiol dicetate; hydroxyprogesterone caproate; medroxyprogesterone acetate; norethindrone acetate; megestrol acetate; and gestogen.

2. The method of claim 1, wherein the rest interval device comprises the same progestin and estrogen and the treatment interval devices.

3. The method of claim 1, wherein the rest interval device has the same hormone concentrations as each treatment interval device but is a fraction of the size of the treatment interval device.

4. The method of claim 1, wherein the rest interval device is the same size as each treatment interval device but comprises reduced amounts of the estrogen and progestin compared to the treatment interval device.

5. The method of claim 1, wherein: (a) the amount of progestin delivered during the rest interval is ¼, ⅓, ½, ⅔ or ¾ of the amount delivered from each treatment interval device during the treatment interval; and (b) the amount of estrogen delivered during the rest interval is ¼, ⅓, ½, ⅔ or ¾ of the amount delivered from each treatment interval device during the treatment interval.

6. The method of claim 1, wherein the rest interval device is worn during all of the rest interval.

7. The method of claim 1, wherein the estrogen in the treatment interval devices and the rest interval device is ethinyl estradiol.

8. The method of claim 1, in which the dosing regimen provides an average serum concentration of about 15 to about 65 pg/ml of ethinyl estradiol during each treatment interval in a given woman or population of women.

9. A kit for use in the method of claim 1, comprising:
(a) three or four, or a multiple of three or four, transdermal hormone delivery treatment interval devices, each treatment interval device comprising a progestin and an estrogen in an amount sufficient to reduce the risk of pregnancy, each being intended for wear for one week; and
(b) one rest interval device for each three or four treatment devices, intended for wear during a rest interval between successive three-week or four-week treatment intervals, wherein the rest interval device comprises: (1) low dose progestin in an amount sufficient to deliver 25% to 75% the amount of the progestin delivered during each week of the treatment interval, and (2) low dose estrogen in an amount sufficient to deliver 25% to 75% the amount of the estrogen delivered during each week of the treatment interval.

10. The kit of claim 9, wherein the rest interval device comprises the same progestin and estrogen as the treatment interval devices.

11. The kit of claim 9, wherein the rest interval device has the same hormone concentrations as each treatment interval device but is a fraction of the size of the treatment interval device.

12. The kit of claim 9, wherein the rest interval device is the same size as the treatment interval device but comprises reduced amounts of estrogen and progestin compared to the treatment interval device.

13. The kit of claim 9, wherein the treatment interval devices and the rest interval device are formulated such that: (a) the amount of progestin delivered during the rest interval is ¼, ⅓, ½, ⅔ or ¾ of the amount delivered from each treatment interval device during the treatment interval; and (b) the amount of estrogen delivered during the rest interval is ¼, ⅓, ½, ⅔ or ¾ of the amount delivered from each treatment interval device during the treatment interval.

14. The kit of claim 9, wherein the estrogen in the treatment interval devices and the rest interval device is ethinyl estradiol.

15. The kit of claim 14, in which the treatment interval devices are formulated to deliver an average serum concentration of about 15 to about 65 pg/ml of ethinyl estradiol during each treatment interval, in a given woman or in a population of women.

* * * * *